United States Patent
Pashkovski et al.

(10) Patent No.: US 8,815,800 B2
(45) Date of Patent: Aug. 26, 2014

(54) MOISTURIZING COMPOSITION COMPRISING AN AMINOPEPTIDE MIXTURE

(71) Applicant: Conopco, Inc., Englewood Cliffs, NJ (US)

(72) Inventors: Eugene Pashkovski, Woodbridge, CT (US); Tamara Litvin, Trumbull, CT (US); Alexander Lips, Parkgate (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/688,949

(22) Filed: Nov. 29, 2012

(65) Prior Publication Data

US 2013/0157957 A1   Jun. 20, 2013

Related U.S. Application Data

(60) Provisional application No. 61/577,954, filed on Dec. 20, 2011.

(51) Int. Cl.
*A61K 8/44* (2006.01)
*A61K 8/64* (2006.01)
*A61Q 19/00* (2006.01)

(52) U.S. Cl.
CPC ... *A61K 8/64* (2013.01); *A61K 8/44* (2013.01); *A61Q 19/007* (2013.01); *A61K 8/442* (2013.01)
USPC .......................................................... 514/8.8

(58) Field of Classification Search
CPC ........... A61K 8/44; A61K 8/64; A61K 8/442; A61K 38/0063; A61K 38/05; A61Q 19/007
See application file for complete search history.

(56) References Cited

U.S. PATENT DOCUMENTS

| | | | |
|---|---|---|---|
| 6,149,924 A | * | 11/2000 | Paul .............................. 424/401 |
| 7,659,233 B2 | | 2/2010 | Hurley et al. |
| 2004/0132667 A1 | | 7/2004 | Lintner |
| 2004/0247631 A1 | | 12/2004 | Kropke |
| 2008/0045479 A1 | * | 2/2008 | Robinson et al. ............... 514/62 |
| 2008/0095732 A1 | | 4/2008 | Osborne |
| 2009/0214607 A1 | * | 8/2009 | Lintner et al. ................ 424/401 |

FOREIGN PATENT DOCUMENTS

| | | |
|---|---|---|
| DE | 4127790 A1 | 2/1993 |
| EP | 1672055 A1 | 6/2006 |
| JP | 07062399 | 8/1993 |
| WO | WO0117486 * | 3/2001 ............... A61K 7/00 |
| WO | WO2010136965 A2 | 12/2010 |

OTHER PUBLICATIONS

PCT International Search Report PCT/EP2012/072972 dated Jun. 17, 2013.
PCT Written Opinion PCT/EP2012/072972 dated Jun. 17, 2013.

* cited by examiner

*Primary Examiner* — Julie Ha
*Assistant Examiner* — Erinne Dabkowski
(74) *Attorney, Agent, or Firm* — Edward A. Squillante, Jr.

(57) ABSTRACT

The invention is directed to skin moisturizing compositions comprising an aminopeptide mixture. The composition replenishes the skins natural moisturization factor and delivers excellent sensory benefits. The composition is not unpleasantly viscous during and after application.

10 Claims, No Drawings

MOISTURIZING COMPOSITION COMPRISING AN AMINOPEPTIDE MIXTURE

FIELD OF THE INVENTION

The present invention is directed to a moisturizing composition comprising an aminopeptide mixture. More particularly, the invention is directed to a moisturizing composition that replenishes the skin's natural moisturization factor while surprisingly delivering excellent sensory benefits. The composition of this invention is not sticky or draggy, has components suitable to penetrate various segments of the stratum corneum and does not become unpleasantly viscous during and after application.

BACKGROUND OF THE INVENTION

The Natural Moisturizing Factor (NMF) of skin contains the components "responsible" for keeping skin healthy and making sure the structure of the epidermis is intact of skin moisturization. NMF exists within the corneocytes in top layers of the stratum corneum, the outer most layer of the epidermis. NMF is a product of proteolysis of filaggrin, which aids self-assembly of keratin intermediate filaments that form the corneocytes. Depletion of NMF in upper layers of the stratum corneum (often associated with skin washing) can induce dry skin conditions, especially in the winter. In other cases, when the gene producing filaggrin protein is mutant, NMF levels in human skin are significantly reduced, leading to severe skin dryness and even dermatological disorders such as atopic dermatitis and Ichthyosis vulgaris.

Regardless of the cause associated with NMF reduction, topical application of compositions designed to mimic NMF is difficult since such compositions are thick upon application, and undesirable for consumer use. In fact, such known compositions result in an unpleasant sticky layer that offers little sensory benefits to consumers in need of skin moisturization.

In view of the above, there is an increasing interest to develop compositions that deliver components to moisturize skin in a manner that mimics the body's NMF. Moreover, it is desirable to develop such so that the same do not comprise high viscosity and unpleasant stickiness characteristics, especially during application and after applying. This invention, therefore, is directed to a moisturizing composition comprising an aminopeptide mixture. The composition mimics and replenishes the skin's NMF while surprisingly delivering excellent sensory benefits. The composition of this invention is not sticky and draggy, has components suitable to penetrate various segments of the stratum corneum and does not become unpleasantly viscous (i.e., sticky) during and after application.

ADDITIONAL INFORMATION

Efforts have been disclosed for making topical skin compositions. In DE 4127790A, skin-care cosmetics having oligopeptide and metal complexes are described.

Other efforts have been disclosed for making topical compositions. In U.S. Pat. No. 7,659,233, personal care compositions with silicones and dihydroxypropyl trialkyl ammonium salts are described.

None of the additional information above describes a composition with an aminopeptide mixture as described in this invention.

Even other efforts have been disclosed for making topical compositions. In U.S. Patent Application No. 2004/0247631, compositions for skin moisturizing are described.

SUMMARY OF THE INVENTION

In a first aspect, the present invention is directed to a composition for moisturizing skin, the composition comprising:
a) an aminopeptide mixture comprising:
  i. water soluble amino acid or functionalized amino acid;
  ii. water soluble dipeptide having a molecular weight from about 150 to about 410;
  iii. water soluble tripeptide having a molecular weight from about 225 to about 600, water soluble vitamin or vitamin derivative comprising peptide bonds or both; and
b) cosmetically acceptable carrier
  wherein amino acid and water soluble dipeptide together make up from 50 to 99% by weight of the total weight of the aminopeptide mixture.

In a second aspect, the present invention is directed to a method of moisturizing skin by applying components that mimic the skin's NMF, the method comprising the step of contacting skin with the composition of the first aspect of this invention.

Skin, as used herein, is meant to include skin on the face, neck, chest, back, arms (including underarms) hands, legs, buttocks and scalp. Water soluble, as used herein, means that at least 0.5 grams of material dissolves in 100 ml of water at 25° C. Comprising, as used herein, is meant to include consisting essentially of and consisting of. For the avoidance of doubt, the aminopeptide mixture of this invention may consist essentially of or consist of amino acid, dipeptide and tripeptide. All ranges identified herein are meant to include all ranges subsumed therein if, for example, reference to the same is not explicitly made.

DETAILED DESCRIPTION OF THE PREFERRED EMBODIMENTS

The only limitation with respect to the amino acid or functionalized amino acid that may be used in this invention is that the same may be used in a topical composition and is water soluble. Typically, the amino acids have a partitioning coefficient defined as log kp from −4.5 to 0; and preferably, from −4.5 to −1; and most preferably, from −4.5 to −2 in n-octanol-water (as described in *Journal of Chromatography*, 216 (198 I) 79-92 Elsevier Scientific Publishing Company, Amsterdam—Printed in The Netherlands CHROM. 14,027).

Preferably, the same have a molecular weight from about 70 to about 225. Illustrative yet non-limiting examples of amino acid or functionalized amino acid suitable for use in this invention include glutamine, aspargine, glycine, glutamic acid, threonine, lysine, alanine, serine, hydroxyproline, N-acetyl-L-tyrosine, N-acetyl-L-hydroxyproline, N-acetyl-L-cysteine, L-ornitine monochloride or a mixture thereof.

With respect to the water soluble dipeptides suitable for use, preferred include glycyl-L-glutamate, glycyl-L-tyrosine, L-alanyl-L-glutamine, glycyl glycine, lysyl lysine, glycyl alanine, glycyl lysine, glycyl histidine, or a mixture thereof.

The tripeptides which are water soluble and suitable for use in this invention include L-glutathione, gamma-L-glutamyl-L-cysteinyl-glycine), S-methylglutathione, glycl-prolyl-glutamic acid, lysyl-tyrosyl-lysine, lysyl-tyrosyl-lysine, glycyl-glycyl-histidine, lysyl-lysyl-lysine or a mixture thereof.

Water soluble vitamin comprising peptide bond which may be used in this invention includes, for example, D-L-panthenol. An example of a water soluble vitamin derivative suitable for use includes calcium pantetheine-S-sulfonate.

In a preferred embodiment, the total weight of amino acid and dipeptide in the aminopeptide mixture is from about 50 to about 80%, and most preferably, from about 60 to about 75% by weight amino acid and dipeptide based on total weight of amino acid, dipeptide and tripeptide in the aminopeptide mixture.

Optimally, amino acid makes up from about 5 to about 50% by weight of the total weight of amino acid, dipeptide and tripeptide in the aminopeptide mixture; and most optionally, 10 to about 30% by weight.

Typically, aminopeptide mixture makes up from about 0.5 to about 35%, and preferably, from about 2 to about 20%, and most preferably, from about 6 to about 12% by weight of the total weight of the composition.

In an especially preferred embodiment the aminopeptide mixture employed in this invention has a glass transition temperature from about −75 to about 15° C., and most preferably, from about −48 to about 12° C., and optionally, from about −40 to about 5° C., including all ranges subsumed therein. In a most optimal embodiment, the glass transition temperature of the aminopeptide mixture is from about −17 to about 2° C. when the water concentration of the aminopeptide mixture ranges from about 9 to about 16%.

Compositions of the present invention will typically include cosmetically acceptable carrier components. Water is the most preferred additional carrier. Amounts of water may range from about 1 to about 99%, and preferably, from about 5 to about 90%, and most preferably, from about 35 to about 80%, and optimally, from about 40 to about 75% by weight, based on total weight of the composition for coloring skin and including all ranges subsumed therein. Ordinarily the compositions of this invention will be water and oil emulsions, most preferably, of the oil-in-water variety. Water-in-oil emulsions, and especially, those generally classified as water-in-oil and high internal phase emulsions are, however, an option. Illustrative examples of the high internal phase emulsions suitable to carry the beads of this invention are described in commonly owned U.S. Patent Application Publication Nos. 2008/0311058 and 2009/0247445, the disclosures of which are incorporated herein by reference.

Other cosmetically acceptable carriers suitable for use in this invention may include mineral oils, silicone oils, synthetic or natural esters, and alcohols. Amounts of these materials may range from about 0.1 to about 50%, and preferably, from about 0.1 to about 30%, and most preferably, from about 1 to about 20% by weight of the composition, including all ranges subsumed therein.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, and preferably, from about 4 to about 5 silicon atoms.

Linear volatile silicone materials generally have viscosities of less than about 5 centistokes at 25° C. while cyclic materials typically have viscosities of less than about 10 centistokes.

Nonvolatile silicone oils useful as carrier material include polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from about 5 to about 100,000 centistokes at 25° C.

An often preferred silicone source is a cyclopentasiloxane and dimethiconol solution.

Among suitable esters are:
(1) Alkenyl or alkyl esters of fatty adds having 10 to 20 carbon atoms like isopropyl palmitate, isopropyl isostearate, isononyl isonanonoate, oleyl myristate, isopropyl myristate, oleyl stearate, and oleyl oleate;
(2) Ether-esters such as fatty acid esters of ethoxylated fatty alcohols;
(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters;
(4) Wax esters such as beeswax, spermaceti, myristyl myristate, stearyl stearate; and
(5) Sterol esters, of which soya sterol and cholesterol fatty acid esters are examples thereof.

Emulsifiers may be present in the composition for moisturizing skin of the present invention. Total concentration of the emulsifier may range from about 0.1 to about 40%, and preferably, from about 1 to about 20%, and most preferably, from about 1 to about 5% by weight of the composition, including all ranges subsumed therein. The emulsifier may be selected from the group consisting of anionic, nonionic, cationic and amphoteric actives. Particularly preferred nonionic actives are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_3$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Cationic emulsifiers that may be used include, for example, palmitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Additional emulsifiers that may be used in this invention include amino acid derived amphiphilic compounds such as sodium dilauramidoglytamide lysine (known also under the tradename Pellicer™ L-30), N-acyl arginine methylester hydrochloride with the acyl group containing from 8 to 14 carbon atoms, and N-alkyl amide and ester derivatives of arginine, histidine, lysine, aspartic acid or glutamic acid containing 8 to 14 carbon atoms.

Other generally preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof.

Preservatives can desirably be incorporated into the compositions for moisturizing skin of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition, including all ranges subsumed therein.

Thickening agents may optionally be included in compositions of the present invention. Particularly useful are the polysaccharides. Examples include starches, beta-glucan, natural/synthetic gums and cellulosics. Representative of the starches are chemically modified starches such as sodium hydroxypropyl starch phosphate and aluminum starch octenylsuccinate. Tapioca starch is often preferred. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes crosslinked polyacrylates such as the Carbomers, polyacrylamides such as Sepigel® 305 and taurate copolymers such as Simulgel EG® and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel® INS100.

Amounts of the thickener, when used, may range from about 0.001 to about 5%, and preferably, from about 0.1 to about 2%, and most preferably, from about 0.2 to about 0.5% by weight of the composition including all ranges subsumed therein.

Conventional humectants may be employed in the present invention. These are generally polyhydric alcohol-type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.5 to 20%, preferably between 1 and 15% by weight of the composition.

Fragrances, colorants, fixatives and abrasives may optionally be included in compositions of the present invention. Each of these substances may range from about 0.05 to about 5%, preferably between 0.1 and 3% by weight.

Turning to the other components including actives suitable for use herein, the same can include opacifiers like $TiO_2$ and ZnO and colorants like iron oxide red, yellow and black. Such opacifiers and colorants typically have a particle size from 50 to 1200 nm, and preferably, from 50 to 350 nm.

To even further enhance skin moisturization, actives classified as cationic ammonium compounds may optionally be used in the compositions of this invention. Such compounds include salts of hydroxypropyltri($C_1$-$C_3$ alkyl)ammonium mono-substituted-saccharide, salts of hydroxypropyltri($C_1$-$C_3$ alkyl)ammonium mono-substituted polyols, dihydroxypropyltri($C_1$-$C_3$ alkyl)ammonium salts, dihydroxypropyldi($C_1$-$C_3$ alkyl)mono(hydroxyethyl)ammonium salts, guar hydroxypropyl trimonium salts, 2,3-dihydroxypropyl tri($C_1$-$C_3$ alkyl or hydroxalkyl)ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.01 to about 30%, and preferably, from about 0.1 to about 15% by weight of the composition.

When cationic ammonium compounds are used, preferred additional active for use with the same are moisturizing agents such as substituted ureas like hydroxymethyl urea, hydroxyethyl urea, hydroxypropyl urea; bis(hydroxymethyl) urea; bis(hydroxyethyl)urea; bis(hydroxypropyl)urea; N,N'-dihydroxymethyl urea; N,N'-di-hydroxyethyl urea; N,N'-dihydroxypropyl urea; N,N,N'-tri-hydroxyethyl urea; tetra(hydroxymethyl)urea; tetra(hydroxyethyl)urea; tetra(hydroxypropyl)urea; N-methyl-N'-hydroxyethyl urea; N-ethyl-N,N-N'-hydroxyethyl urea; N-hydroxypropyl-N'-hydroxyethyl urea and N,N'-dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea, when used, in the composition of this invention range from about 0.01 to about 20%, and preferably, from about 0.5 to about 15%, and most preferably, from about 2 to about 10% based on total weight of the composition and including all ranges subsumed therein.

When cationic ammonium compound and substituted urea are used, in a most especially preferred embodiment at least from about 1 to about 15% glycerin external to the particle is used, based on total weight of the composition and including all ranges subsumed therein.

Compositions of the present invention may include vitamins as the desired active. Illustrative vitamins are Vitamin A (retinol) as well as retinol esters like retinol palmitate and retinol propionate, Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. Total amount of vitamins when present in compositions according to the present invention may range from 0.001 to 10%, preferably from 0.01% to 1%, optimally from 0.1 to 0.5% by weight of the composition.

Octadecenedioic acid, azelaic acid, ubiquinone, dihydroxyacetone (DHA) and mixtures thereof may also be used as actives in the composition of this invention. Such compounds, when used, typically make up from about 0.2 to 4.5%, and preferably, from about 0.5 to 3% by weight of the composition, including all ranges subsumed therein.

Other optional actives suitable for use in this invention include resveratrol, resorcinols like 4-ethyl resorcinol, 4-hexyl resorcinol, 4-phenylethyl resorcinol, dimethoxytoluyl propyl resorcinol, 4-cyclopentyl resorcinol, 4-cyclohexylresorcinol, alpha- and/or beta-hydroxyacids, petroselinic acid, conjugated linoleic acid, octadecanoic acid, phenylethyl resorcinol (Symwhite 377 from Symrise), undecylenol phenylalanine (Seppi White from Seppic) mixtures thereof or the like. Such actives, when used, collectively make up from about 0.001 to about 12% by weight of the composition.

Desquamation promoters may be present. Illustrative are the alpha-hydroxycarboxylic acids, beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic and its derivatives, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary. Soy extracts may be used and especially when it is desirable to include retinol.

Also optionally suitable for use include materials like chelators (e.g., EDTA), $C_{8-22}$ fatty acid substituted saccharides, lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Occlusives like Oilwax LC are often desired. Amounts of these materials may range from about 0.000001 to about 10%, preferably from about 0.0001 to about 1% by weight of the composition.

Sunscreen actives may also be included in compositions of the present invention and carried by the particle comprising hydrophobic material as described herein. Particularly preferred are such materials as phenylbenzimidazole sulfonic acid (Ensulizole), ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide, zinc oxide, polyethylene and various other polymers. Also suitable for use is octocrylene. Amounts of the sunscreen agents when present may generally range from 0.1 to 30%, preferably from 0.5 to 20%, optimally from 0.75 to 10% by weight.

Conventional buffers/pH modifiers may be used. These include commonly employed additives like sodium hydroxide, potassium hydroxide, hydrochloric acid, citric acid and citrate/citric acid buffers. In an especially preferred embodiment, the pH of the composition of this invention is from about 4 to about 8, and preferably, from about 4.25 to about 7.75, and most preferably, from about 6 to about 7.5, including all ranges subsumed therein. The composition of this invention may be a solid stick or bar. Viscosity of the composition of this invention is, however, preferably from about 1,000 to about 120,000 cps, and most preferably, from about 5,000 to 80,000 cps, taken at ambient temperature and a shear rate of $1\ s^{-1}$ with a strain controlled parallel plate rheometer made commercially available from suppliers like T.A. Instruments under the ARES name.

A wide variety of packaging can be employed to store and deliver the composition of this invention. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

When applying composition of this invention topically, typically from about 0.5 to about 5 mg of composition is applied per $cm^2$ of skin.

The following examples are provided to facilitate an understanding of the present invention. The examples are not intended to limit the scope of the claims.

Example 1

The compositions in the following examples were made by combining the ingredients indentified below. The compositions were made by mixing the ingredients with moderate shear under conditions of atmospheric pressure and ambient temperature.

| Ingredient | Sample 1 Weight percent | Sample 2 Weight percent |
|---|---|---|
| Glutamine | 1.39 | — |
| Aspargine | 1.11 | — |
| Glycine | 1.39 | 5.73 |
| Glutamic acid | 0.56 | — |
| Threonine | 1.94 | — |
| Lysine | 1.11 | — |
| Alanine | 1.67 | 4.11 |
| Serine | 0.83 | 12.13 |
| Pyrrolidone carboxylic acid | — | 8.03 |
| Arginine | — | 2.75 |
| Citrulline | — | 2.75 |
| Histidine | — | 6.31 |
| Water | Balance | Balance |

| Ingredient | Sample 3 Weight percent | Sample 4 Weight percent | Sample 5 Weight percent | Sample 6 Weight percent |
|---|---|---|---|---|
| N-acetyl-L-hydroxyproline | 2.22 | 2.5 | 2.5 | 2.5 |
| L-alanyl-L-Glutamate | 2.22 | 2.5 | 3.75 | 2.5 |
| Glycyl Glycine | 2.22 | 2.5 | 2.5 | 3.75 |
| L-Glutathione | 3.33 | 2.5 | 1.25 | 1.25 |
| Water | Balance | Balance | Balance | Balance |

Other Examples

| Ingredient | Weight percent |
|---|---|
| *Sample 7* | |
| Glutamine | 1.39 |
| Aspargine | 1.11 |
| Glycine | 1.39 |
| Glutamic acid | 0.56 |
| Threonine | 1.94 |
| Lysine | 1.11 |
| Alanine | 1.67 |
| Serine | 0.83 |
| Sunflower oil | 3 |
| Tinocare gel | 10 |
| Pellicer | 0.3 |
| Water | Balance |
| *Sample 8* | |
| N-acetyl-L-hydroxyproline | 2.22 |
| L-alanyl-L-Glutamate | 2.22 |
| Glycyl Glycine | 2.22 |
| L-Glutathione (Reduced) | 3.33 |
| Sunflower oil | 3 |
| Tinocare gel | 10 |
| Pellicer | 0.3 |
| Water | Balance |
| *Sample 9* | |
| Glutamine | 1.39 |
| Aspargine | 1.11 |
| Glycine | 1.39 |
| Glutamic acid | 0.56 |
| Threonine | 1.94 |
| Lysine | 1.11 |
| Alanine | 1.67 |
| Serine | 0.83 |
| Trehalose | 1 |
| Sunflower oil | 3 |
| Xanthan | 1 |
| Water | Balance |

| Ingredient | Sample 10 Weight percent | Sample 11 Weight percent |
|---|---|---|
| N-acetyl-L-hydroxyproline | 2.22 | 2.22 |
| L-alanyl-L-Glutamate | 2.22 | 2.22 |
| Glycyl Glycine | 2.22 | 2.22 |
| L-Glutathione Reduced | 2.33 | — |
| Calcium pantetheine-S-sulfonate | — | 2.33 |
| L-Glutathione (Oxidized) | 1.0 | 1.0 |
| Trehalose | 1 | 1 |
| Sunflower oil | 3 | 3 |
| Xanthan | 1 | 1 |
| Water | Balance | Balance |

Example 2

Skin Moisturization

Skin moisturization was assessed in terms of hydration, measured using a Corneometer (Courage+Khazaka, Germany, model CM 825, consistent with the Sorption Desorption Test described in *Bioengineering of the Skin:Water and the Stratum Corneum*, by G. Borroni et al., Ed by P. Elsner et al., CBC Press, Chapter 18, 1995). Instrument readings typically vary from 5 to 120 units, with small numbers (~6) typical for nails, higher numbers typical for dry skin (~10-20), medium numbers typical for hydrated skin (~40) and large numbers typical for skin immediately after application of water-based humectants (above 100).

Ex-vivo porcine skin (area 1.5 cm×1.5 cm) was treated with 0.1 ml of the compositions identified in Table 1 as well as a 10% glycerol solution and deionized water as the control. Readings were taken before treatments as a baseline and at least 5 measurements were made at the same position at the time intervals shown in the table.

The relative hydration numbers were calculated as 100%* $(C_t-C_0)/C_0$, where $C_0$ is the reading before the treatment, and $C_t$ is the reading taken at the time t after treatment.

The change in hydration with respect to the initial hydration number for a given area of skin after 10, 30, and 60 minutes of composition application to model skin was found to be maximal for the aminopeptide containing composition of Sample 3 which is made consistent with this invention. When only a combination of water soluble amino acids was used (Sample 1), skin hydration was lower as was skin hydration observed for glycerol.

TABLE 1

| Composition Time (minutes) | (Sample 3) | (Sample 1) | Glycerol (10%) | Deionized Water |
|---|---|---|---|---|
| | | Relative Hydration (percent) | | |
| 10 | 55 | 13.1 | 23 | 21 |
| 30 | 42 | 15.5 | 11 | 4.6 |
| 60 | 40 | 16 | 10 | 4 |

The results in this table unexpectedly demonstrate that when compositions made consistent with this invention are applied, excellent moisturization results are obtained.

Example 3

Glass Transition Temperature

Glass transition temperatures were measured using differential scanning calorimetry (DSC Q1000, TA Instruments) at a heating rate of 10 K/min from −80 to +40° C. Glass transition temperatures were determined using TA instrument software (TA Advantage) from the middle of the heat capacity curve. The compositions comprising aminopeptide mixtures consistent with this invention were assessed against glycerol and other compositions with amino acids. Table 2 below depicts the glass transition temperatures of the compositions assessed. Water concentration means the water concentration of the composition at the time the glass transition temperature was obtained. Water was evaporated from contained compositions by storing the same at room temperature at a relative humidity of about 33%.

TABLE 2

| Water concentration (% in composition at reading) | Sample 3 | Sample 2 | Sample 4 | Samples 5 | Glycerol |
|---|---|---|---|---|---|
| 40 | — | — | — | — | −108 |
| 23 | −50 | −67 | −68.26 | — | — |
| 19 | −33 | −50 | −56.42 | — | — |
| 15 | −16 | −37 | −44.58 | — | — |
| 10.3 | — | — | — | −36.4 | — |
| 10 | 3 | −21 | −29.77 | — | — |
| 9.6 | — | — | — | −11.5 | — |
| 8.7 | 14 | −9 | −25.92 | 2.4 | — |
| 0 | — | — | — | — | −83 |

The data in Table 2 shows, unexpectedly, that compositions made according to this invention will yield a consumer desirable glassy film that results in excellent water retention. For Sample 6, glass transition temperatures observed were similar to those of Sample 5. In the samples not consistent with this invention, rapid water evaporation (i.e., poor moisturization) is observed.

Example 3

Hydration of Stratum Corneum

The hydration of the stratum corneum was estimated from hysteresis observed during the sorption-desorption cycle. Disks of stratum corneum (6 mm in diameter) were treated with 0.06 mL aminopeptide mixture, glycerol or water at both sides and dried. The samples were then placed in a Dynamic Water Sorption Analyzer and with controlled humidity. When the humidity was increased in small steps (Delta RH=10%) water uptake was measured after 3 hours equilibration for each step. Water uptake is defined as a mass of water per the dry mass of stratum corneum.

Table 3 depicts the values of water uptake for sorption and desorption for stratum corneum treated with aminopeptide mixture consistent with this invention (Sample 3), glycerol and stratum corneum treated with deionized water. The difference between the water uptake at sorption and desorption shows the degree of moisturization at given experimental conditions.

TABLE 3

(results for Sample 3)

| Relative humidity, % | Water uptake, mg/g-sorption | Water uptake, mg/g-desorption | Water uptake difference in mg/g |
|---|---|---|---|
| 20 | 26.97 | 39.63 | 12.66 |
| 30.8 | 48.98 | 57.79 | 8.81 |
| 40.8 | 73.75 | 105.12 | 31.37 |
| 50.7 | 103.47 | 146.84 | 43.37 |
| 61 | 144.74 | 208.42 | 63.68 |
| 71 | 206.93 | 264 | 57.07 |

The data in Table 3 unexpectedly shows high water uptake at high relative humidity, meaning excellent water retention and moisturization results.

TABLE 4

(results for glycerol (10%) and water treatment, 0.12 mL applied)

| Relative humidity % | Water uptake mg/g-sorption | Water uptake mg/g-desorption | water uptake difference in mg/g (desorption-sorption) |
|---|---|---|---|
| 10% Glycerol treatment ||||
| 20.8 | 122.22 | 87.3 | 34.92 |
| 31 | 161.38 | 135.34 | −26.04 |
| 41 | 209.84 | 192.06 | −17.78 |
| 51 | 275.13 | 261.90 | −13.23 |
| 60.2 | 366.67 | 366.67 | 0 |
| 70.35 | 524.34 | 524.34 | 0 |
| Water treatment ||||
| 20 | 23 | 25 | 2 |
| 27 | 30 | 35.8 | 5.8 |
| 34 | 37.4 | 43 | 5.6 |
| 41 | 45.7 | 51 | 5.3 |
| 47 | 53.9 | 59 | 5.04 |
| 54 | 63.8 | 69.9 | 6.1 |
| 61 | 78 | 82.6 | 4.6 |

The results in Table 4 demonstrate, surprisingly, that water retention and moisturization is significantly better for the compositions made consistent with this invention.

Example 4

Viscosity Measurements

Viscosity of aminopeptide mixtures consistent with this invention and amino acid mixtures were measured at different temperatures and concentrations of water using standard plate-plate geometry (25 mm) in an oscillatory deformation regime at frequency 1 Rad/s with amplitudes ranging from 0.1 to 10% depending on the sample viscosity. The dynamic viscosity under these conditions is defined as the loss modulus G″ divided by the frequency of oscillatory deformation. The increase in viscosity at low water concentrations indicates the stickiness and unattractiveness of the formula on skin. When composition dries and the water concentration drops lower than 20%, composition not consistent with this invention (Sample 2) leads to the formation of viscous films on skin whereas the viscosity of the composition having aminopeptide mixture consistent with this invention in (Sample 3) yields a lower and desirable viscosity. This behavior unexpectedly results in a composition that is less sticky or draggy.

TABLE 5

| | Dynamic Viscosity, Pa * s | |
|---|---|---|
| Water weight fraction (%) | NMF (Sample 2) | (Sample 3) |
| 7.35 | 8184.5 | 1456 |
| 9 | 1878.1 | 255 |
| 11.6 | 317.3 | 33 |
| 12.44 | 68.03 | 15 |
| 15.8 | 9.73 | 3.7 |
| 17.5 | 4.39 | 2.29 |
| 20 | 1.28 | 1.5 |
| 27 | 0.23 | 0.8 |
| 15.8 | 9.73 | 3.7 |

The results in Table 5 unexpectedly reveal that composition comprising aminopeptide mixtures consistent with this invention do not become thick and sticky subsequent to water loss.

Compositions made consistent with this invention (including those described in Samples 7-11) were topically applied to skilled panelist and all concluded that the compositions were easy to apply and not sticky during and after application. All panelists further concluded that such compositions yielded sensory results consistent with excellent moisturization.

What is claimed is:
1. A skin composition comprising:
  a) From 2% to 20% by weight of total composition an aminopeptide mixture-comprising:
    i. a functionalized amino acid which is N-acetyl-L-hydroxyproline;
    ii. a water soluble dipeptide mixture comprising L-alanyl-L-glutamate and glycyl glycine;
    iii. a water soluble tripeptide which is L-glutathione;
  wherein the functionalized amino acid and water soluble dipeptide mixture together make up from 50 to 99% by weight of the total weight of the aminopeptide mixture; and
    wherein the aminopeptide mixture has a glass transition temperature from about −75 to about 15° C. and;
  b) a cosmetically acceptable carrier.
2. The skin composition according to claim 1 further comprising calcium pantetheine-S-sulfonate.

3. The skin composition according to claim 1 wherein the total weight of functionalized amino acid and dipeptide mixture in the aminopeptide mixture is from about 50 to 80% based on the weight of the aminopeptide mixture.

4. The skin composition according to claim 1 wherein the functionalized amino acid makes up from about 5 to about 50% by weight of the aminopeptide mixture.

5. The skin composition according to claim 1 wherein the aminopeptide mixture has a glass transition temperature from about −48 to about 12° C.

6. The skin composition according to claim 1 wherein the composition further comprises niacinamide.

7. The skin composition according to claim 1 wherein the composition further comprises a cationic ammonium compound, substituted urea, glycerol or a mixture thereof.

8. The skin composition according to claim 1 wherein the composition further comprises sunscreen, a resorcinol or a mixture thereof.

9. The skin composition according to claim 1 wherein the composition further comprises water, silicone and emulsifier.

10. A method for moisturizing skin by replenishing natural moisturization factor of skin, the method comprising the step of topically applying to skin the composition of claim 1.

* * * * *